United States Patent [19]

Dusza et al.

[11] 4,360,680

[45] Nov. 23, 1982

[54] THERAPEUTICALLY ACTIVE 3-AMINO-1-PHENYL AND SUBSTITUTED PHENYL-2-PYRAZOLINES

[75] Inventors: John P. Dusza, Nanuet, N.Y.; Joseph P. Joseph, Montvale, N.J.; Seymour Bernstein, New City, N.Y.

[73] Assignee: American Cyanamid Company, Stamford, Conn.

[21] Appl. No.: 282,905

[22] Filed: Jul. 13, 1981

[51] Int. Cl.³ ......................................... C07D 231/06
[52] U.S. Cl. ............................... 548/362; 424/273 P
[58] Field of Search ........................................ 548/362

[56] References Cited

U.S. PATENT DOCUMENTS 2,726,248  12/1955  Kendall et al. ..................... 548/362
4,149,005  4/1979  Battisti et al. ....................... 548/362

OTHER PUBLICATIONS

Duffin et al., Chem. Abst. 1955, vol. 49, p. 10270c.
Kost et al., Zhurnal Obshckey Khimii 1959, vol. 29(2), pp. 498-502.

Primary Examiner—Henry R. Jiles
Assistant Examiner—N. Harkaway
Attorney, Agent, or Firm—Anne M. Rosenblum

[57] ABSTRACT

A method of treating pain, meliorating inflammation in warm-blooded animals as well as a method for treating fungal and bacterial infections in such animals using certain 3-amino-1-phenyl-2-pyrazolines and 3-amino-1-substituted phenyl-2-pyrazolines and their C4 and C5 analogs, as well as compounds used in the above are disclosed.

3 Claims, No Drawings

THERAPEUTICALLY ACTIVE 3-AMINO-1-PHENYL AND SUBSTITUTED PHENYL-2-PYRAZOLINES

PRIOR ART

Related references:

1. R. Battisti, et. al., U.S. Pat. No. 4,149,005 (Apr. 10, 1979) describes compounds of the formula:

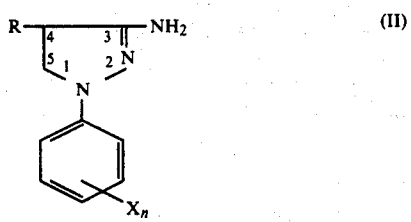

where R is H or $CH_3$, X is H, Br, Cl, alkyl, alkoxy or carboxyalkyl groups with from 1 to 4 carbon atoms or $CF_3$; and n is 1 or 2. Battisti used these compounds as intermediates in the preparation of 1-phenyl-3-aminopyrazoles used as coupling components in azo dye manufacture. Related foreign patents are: Ger. Offen. Pat. No. 2,727,706; French Pat. No. 2,355,834; Gr. Br. 1,515,500; Belgium Pat. No. 855,944; Netherland Pat. No. 7,706,760 and Japan 28,168.

2. G. A. Higgs, et al.; (Wellcome Research Laboratories); Biochemical Pharmacology, 28 1959 (1979) describes 3-amino-1-[m-(trifluoromethyl)phenyl]-2-pyrazoline (BW 755C) of the formula:

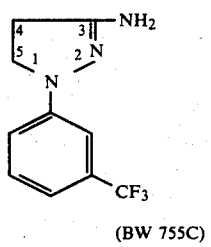

(BW 755C)

This compound is reported to have anti-inflammatory activity.

DESCRIPTION OF THE INVENTION

This invention is concerned with a method of treating pain, meliorating inflammation, as well as a method for the control of fungal and bacterial infections in such animals which comprises the administration of certain 3-amino-1-phenyl-2-pyrazoline and 3-amino-1-substituted phenyl-2-pyrazoline compounds of the formula I:

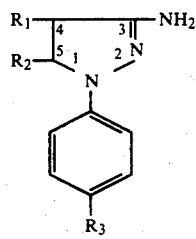

wherein $R_1$ is hydrogen and lower alkyl ($C_1$–$C_4$); $R_2$ is hydrogen, lower alkyl ($C_1$–$C_4$), phenyl and

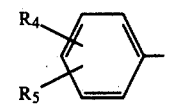

where $R_4$ and $R_5$ may be the same or different and may be selected from the group comprising hydrogen, halogen, and lower alkyl ($C_1$–$C_4$); $R_3$ is hydrogen, lower alkyl ($C_1$–$C_4$); carboxy, methoxy, trifluoromethylcarbonyl and phenyl and the pharmacologically acceptable acid-addition salts thereof.

The compounds of Formula I where $R_2$ is hydrogen and $R_3$ is other than hydrogen, or lower alkyl or methoxy; or where $R_2$ is other than hydrogen are novel compounds.

This invention is also concerned with a method of treating pain using a quaternary salt of the formula II:

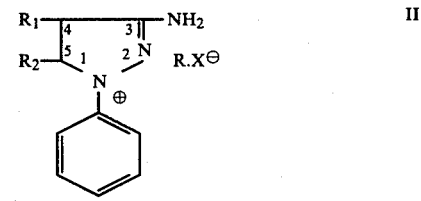

wherein R is lower alkyl ($C_1$–$C_4$); $R_1$ and $R_2$ may be hydrogen and lower alkyl ($C_1$–$C_4$) and X is halogen.

The novel compounds of this invention and the compounds used in this invention are prepared by the adaption of the procedure of Duffin, G. F. and Kendall, J. D., J. Chem. Soc. 1954, 408 by base catalyzed condensation of the appropriate hydrazine with the appropriate acrylonitrile compound. The 2-pyrazolines which are formed can be converted into other derivatives of this invention by procedures known per se.

It has been discovered that some of the compounds generically described above possess activity as analgetic agents when tested by the "writhing syndrome" test for analgesic activity as described by Siegmund, et al., Proc. Soc. Exp. Biol. and Med., 95, 729 (1957), with modifications. The following representative compounds of the present invention have been shown to possess analgesic activity by this test:

3-Amino-1-phenyl-2-pyrazoline
3-Amino-1-p-tolyl-2-pyrazoline
3-Amino-5-(3,4-dichlorophenyl)-1-phenyl-2-pyrazoline
3-Amino-5-(p-chlorophenyl)-1-phenyl-2-pyrazoline
3-Amino-1,4-dimethyl-1-phenyl-2-pyrazolinium iodide Representative compounds of this invention have proven to be active in vivo as anti-inflammatory agents when tested by the Carrageenin Induced Edema of the Rat Paw Test. This test is a modification of the method of Winter, C. A., et al., Proc. Soc. Exp. Biol. and Med., 111, 544 (1962). Compounds found to be active in this test are:

3-Amino-1-phenyl-2-pyrazoline hydrochloride
3-Amino-5-methyl-1-phenyl-2-pyrazoline
3-Amino-4-methyl-1-phenyl-2-pyrazoline
3-Amino-1-phenyl-5-p-tolyl-2-pyrazoline
3-Amino-5-ethyl-1-phenyl-2-pyrazoline Representative compounds of the present invention have been proven active in vitro as antibacterial and/or antifungal agents when tested by such procedures as the standard agar dilution procedure. Compounds found to be active in these tests are:

3-Amino-1-phenyl-2-pyrazoline
3-Amino-1-phenyl-2-pyrazoline hydrochloride
3-Amino-5-methyl-1-phenyl-2-pyrazoline
3-Amino-4-methyl-1-phenyl-2-pyrazoline
3-Amino-1,5-diphenyl-2-pyrazoline
3-Amino-1-phenyl-5-p-tolyl-2-pyrazoline
3-Amino-1-p-tolyl-2-pyrazoline
3-Amino-1-(4-biphenylyl)-5-methyl-2-pyrazoline
3-Amino-1-phenyl-2-pyrazoline sulfate (2:1)
3-Amino-5-(3,4-dichlorophenyl)-1-phenyl-2-pyrazoline
3-Amino-5-(p-chlorophenyl)-1-phenyl-2-pyrazoline
3-Amino-1-(p-methoxyphenyl)-5-phenyl-2-pyrazoline
3-Amino-5-ethyl-1-phenyl-2-pyrazoline
4'-(3-Amino-4-methyl-2-pyrazolin-1-yl)-2,2,2-trifluoroacetophenone The active compounds of the present invention have been found to be useful for treating pain, meliorating inflammation in warm-blooded animals, as well as treating bacterial and fungal infections in such animals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 mg. to about 7.0 gm. of the active ingredient for a subject of about 70 kg. of body weight are administered in a 24 hour period. This dosage regimen may be adjusted to provide the optimum therapeutic response. For example, several divided doses may be administered dialy or the dose may be proportionally reduced as indicated by the exigencies of the therapeutic situation. A decided practical advantage of this invention is that the active ingredient may be administered in any convenient manner such as by the oral, intravenous, intramuscular, intra-articular, topical, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

This invention will be described in greater detail in conjunction with the following examples.

EXAMPLE 1

3-Amino-1-phenyl-2-pyrazoline

A 2.0 g. amount of sodium metal is dissolved in 100 ml. of absolute ethanol, then 40.0 ml. of phenylhydrazine is added followed by 26.0 ml. of acrylonitrile. The reaction mixture is refluxed for 3 hours with exothermic crystallization of a product. The product is collected by filtration and washed with 95% ethanol. The material is recrystallized from dichloromethane-benzene to give 43.6 g. of the desired product as a solid, m.p. 168°–170.5° C.

EXAMPLE 2

3-Amino-1-phenyl-2-pyrazoline hydrochloride

A 2.0 g. amount of 3-amino-1-phenyl-2-pyrazoline (Example 1) is dissolved in 15 ml. of concentrated hydrochloric acid, then is poured into anhydrous ethyl ether to crystallize a product. The product is collected by filtration and recrystallized from acetone-hexane to give 1.50 g. of the desired product as a white solid, m.p. 94°–96° C.

EXAMPLE 3

3-Amino-5-methyl-1-phenyl-2-pyrazoline

A 2.0 g. amount of sodium metal is dissolved in 200 ml. of absolute ethanol, then 32.4 g. of phenylhydrazine in 50 ml. of ethanol is added followed in 10 minutes by 20.1 g. of crotononitrile. The reaction mixture is refluxed for 5 hours. Most of the ethanol is removed in vacuo, water is added and the product is collected by filtration. The solid is dissolved in dichloromethane. This solution is passed through a short column of a hydrous magnesium silicate. The column effluent is then refluxed on a steam bath with the gradual addition of hexane to crystallize a product. The product is collected and recrystallized from acetone-hexane to give 26.9 g. of the product of the Example as colorless prisms, m.p. 103.5°–106° C.

EXAMPLE 4

3-Amino-4-methyl-1-phenyl-2-pyrazoline

A 2.0 g. amount of sodium metal is dissolved in 200 ml. of absolute ethanol, then 37.4 g. of phenylhydrazine is added followed in 10 minutes by 20.1 g. of methacrylonitrile. The reaction mixture is refluxed for 4 hours then is evaporated to near dryness in vacuo. Water is added to the residue to separate an oil. The oil crystallizes on standing. The solid is dissolved in dichloromethane. The solution is passed through a short column of a hydrous magnesium silicate. The column effluent is evaporated to give an oil. The oil is crystallized from acetone-hexane then is recrystallized from the same solvent pair to give 20.88 g. of the desired product as colorless crystals, m.p. 83°–84° C.

EXAMPLE 5

3-Amino-1,4-dimethyl-1-phenyl-2-pyrazolinium iodide

A 6.0 g. amount of 3-amino-4-methyl-1-phenyl-2-pyrazoline (Example 4) and 12.0 ml. of methyl iodide is heated at reflux for 2 hours. The reaction mixture is cooled and filtered to collect 11.2 g. of crude product. The material is dissolved in water and recrystallized from 95% ethanol to give 4.5 g. of the product of the Example as colorless needles, m.p. 168.5°–170° C.

EXAMPLE 6

3-Amino-1,5-diphenyl-2-pyrazoline

A 2.0 g. amount of sodium metal is dissolved in 150 ml. of absolute ethanol, then 40.0 ml. of phenylhydrazine is added followed in 5 minutes by 48.0 ml. of cinnamonitrile. The reaction mixture is refluxed for 3 hours with exothermic crystallization of a product. The product is collected by filtration and washed with water. The material is recrystallized from absolute ethanol to give 56.0 g. of the desired product as a solid, m.p. 195°–197° C.

EXAMPLE 7

3-Amino-1-phenyl-5-p-tolyl-2-pyrazoline

A 1.0 g. amount of sodium metal is dissolved in 100 ml. of absolute ethanol, then 20.0 ml. of phenylhydrazine is added followed in 5 minutes by 24.0 ml. of (mixed cis and trans) 4-methyl cinnamonitrile. The reaction mixture is refluxed for 4 hours then is cooled. The precipitate is collected by filtration then is recrystallized from acetone-hexane after treatment with activated charcoal to give 14.25 g. of the desired product as pale orange needles, m.p. 165°–166.5° C.

EXAMPLE 8

3-Amino-1-p-tolyl-2-pyrazoline

A 2.8 g. amount of sodium metal is dissolved in 150 ml. of absolute ethanol, then 15.86 g. of p-methylphenylhydrazine hydrochloride is added followed in 5 minutes by 5.5 g. of acrylonitrile. The reaction mixture is refluxed for 18 hours, then is evaporated to dryness in vacuo. Water is added and the separated solid is collected by filtration. The solid is dissolved in dichloromethane and passed through a short column of a hydrous magnesium silicate. The effluent is refluxed with the gradual addition of hexane to separate a crystalline product. The entire crystallization step is repeated to give 3.4 g. of the product of the Example as colorless plates, m.p. 142°–143° C.

EXAMPLE 9 p-(3-Amino-5-phenyl-2-pyrazolin-1-yl)benzoic acid

A 5.0 g. amount of 3-amino-1,5-diphenyl-2-pyrazoline (Example 6) and 20 ml. of trifluoroacetic anhydride is heated until solution is achieved. The reaction mixture is allowed to stand 30 minutes then the precipitate is removed by filtration. The filtrate is allowed to stand for 15 hours and the precipitate which settles out is collected and dissolved in dichloromethane. This solution is passed through a short column of a hydrous magnesium silicate. The effluent is evaporated to dryness in vacuo. The residue is dissolved in acetone and refluxed with the gradual addition of hexane until crystallization occurs. The mixture is cooled and filtered to give 5.3 g. of 2,2,2-trifluoro-N-[5-phenyl-1-(p-trifluoroacetylphenyl)-2-pyrazolin-3-yl]acetamide as yellow needles.

A mixture of 5.3 g. of the preceding product, 100 ml. of acetone, 100 ml. of water and 5.0 g. of pulverized potassium hydroxide is refluxed for 1.5 hours. The reaction mixture is evaporated to dryness in vacuo. Water is added to the residue and the mixture is extracted with dichloromethane and acidified with 5% hydrochloric acid to give a precipitate which is collected by filtration and dried. The solid is treated with ammonium hydroxide and activated charcoal and filtered. The filtrate is acidified with acetic acid to give 0.23 g. of the product of the Example as a yellow solid, m.p. 245°–248° C.

EXAMPLE 10

4'-(3-Amino-5-phenyl-2-pyrazolin-1-yl)-2,2,2-trifluoroacetophenone

A solution of 1.0 g. of 2,2,2-trifluoro-N-[5-phenyl-1-(p-trifluoroacetylphenyl)-2-pyrazolin-3-yl]acetamide (prepared as described in Example 9) in 100 ml. of methanol is saturated with ammonia gas, then is stored in a refrigerator for 16 hours. The solution is evaporated to dryness *in vacuo*. The residue is chromatographed by preparative column chromatography using silica gel and eluting with acetone:hexane, 50:50, to collect the most polar product. The product is recrystallized from dichloromethanehexane to yield 0.25 g. of the product of the Example as yellow needles, m.p. 214°–216° C.

EXAMPLE 11

3-Amino-1-(4-diphenylyl)-5-methyl-2-pyrazoline

A 5.0 g. amount of 4-amino-biphenyl is suspended in a stirred solution of 40.0 ml of concentrated hydrochloric acid and 27.0 ml. of water maintained at 5° C. Stirring is continued and the temperature is maintained below 10° C. during the slow addition of a solution of 8.0 g. of sodium nitrite in 16.0 ml. of water. The reaction mixture is stirred for 15 minutes longer at 5° C. then is added slowly to a cooled solution (0°–5° C.) of 53.0 g. of stannous chloride in 53.0 ml. of concentrated hydrochloric acid. The resulting mixture is diluted with water and treated with a 40% solution of sodium hydroxide until alkaline. The solid formed is collected by filtration, dissolved in dichloromethane, dried over magnesium sulfate and filtered. The filtrate is passed through a short column of a hydrous magnesium silicate. The effluent is evaporated *in vacuo* to give a solid. The solid is dissolved in dichloromethane. This solution is heated to boiling and hexane is added until turbidity occurs. The mixture is cooled and filtered to give 8.5 g. of 4-biphenylhydrazine as orange crystals, m.p. 135°–138° C. (dec.).

A 4.3 g. amount of the preceding compound is added to a solution of 0.1 g. of sodium metal dissolved in 100 ml. of absolute ethanol. Then 1.54 g. of crotononitrile is added and the mixture is refluxed for 6 hours and poured into water to separate a dark solid. The solid is collected, dissolved in dichloromethane and heated to boiling while adding hexane until turbidity results. The mixture is cooled and filtered to give 3.6 g. of the product as a solid. The recrystallization step is repeated to give the product of the Example, m.p. 174°–176° C.

EXAMPLE 12

3-Amino-5-isopropyl-1-phenyl-2-pyrazoline

A mixture of 18.9 g. of isobutyraldehyde and 75.0 g. of cyanomethyltriphenylphosphorane in 500 ml. of dry benzene is refluxed with stirring under nitrogen for 6 hours. The reaction mixture solvents are removed in vacuo in a water bath maintained at 46°–50° C. The solid is removed by filtration and washed with ether then hexane. The filtrate and washings are combined and concentrated leaving a liquid and solid. This material is distilled through a vigreaux column to give 11.03 g. of 4-methyl-2-pentenonitrile as a colorless liquid, b.p. 70°–72° C./45 mm.

A 0.31 g. amount of sodium metal is dissolved in 150 ml. of absolute ethanol, then 6.3 g. of phenylhydrazine is added followed by 5.5 g. of 4-methyl-2-pentenonitrile. The reaction mixture is refluxed for 16 hours. The solvent is removed in vacuo, water is added to the residue and the mixture is extracted with dichloromethane. The extract is dried over anhydrous magnesium sulfate and evaporated to give a gum. The gum is chromatographed on a column containing 400 g. of a synthetic magnesium silicate absorbent. The column is eluted first with portions of 2½% acetone-hexane and 5% acetone-hexane to remove exteraneous colored material, then with portions of 2½% and 10% acetone-hexane to remove the product. The product cuts are evaporated to give 2.7 g. of a dark gum which solidifies on standing. This material is recrystallized twice from ether-hexane to give 1.7 g. of the product of the Example as tan crystals, m.p. 115°–117° C.

EXAMPLE 13

3-Amino-1-phenyl-2-pyrazoline sulfate (2:1)

A 2.0 g. amount of 3-amino-1-phenyl-2-pyrazoline (Example 1) is dissolved in 200 ml. of absolute ethanol, then 4.0 ml. of 10% w/w sulfuric acid solution is added with stirring. The reaction mixture is allowed to stand for 2 hours at room temperature then is filtered. The precipitate is refluxed with 100 ml. of acetone, cooled and filtered to give 1.40 g. of the desired product, m.p. 181°–183° C.

EXAMPLE 14

3-Amino-1-phenyl-5-propyl-2-pyrazoline

A mixture of 10.8 g. of freshly distilled butyraldehyde, 30.9 g. of malonmonoamide, 25 ml. of pyridine and 5 drops of piperadine in a 100 ml. round bottom flask is heated under reflux for 24 hours in an oil bath maintained at 85°–95° C. The reaction mixture is evaporated to dryness in vacuo. The residue is diluted with 10 ml. of water and extracted with five 50 ml. portions of ether. The extracts are combined, dried over anhydrous magnesium sulfate, filtered and evaporated to give a gummy solid. The solid is recrystallized from ether-hexane to give 4.6 g. of 2-hexenamide as white crystals, m.p. 115°–117° C.

A mixture of 5.9 g. of the preceding compound (prepared as described above) and 8.7 g. of phosphorus pentoxide in a 100 ml. round bottom flask with distillation head attached is gradually heated to 200° C. in an oil bath. The mixture is heated at 200° C. for ½ hour, then the pressure is reduced to 50 mm. and heating is continued, gradually lowering the pressure to 15 mm. The distillate is collected in a flask cooled in dry ice to obtain 2.7 g. of 2-hexenecarbonitrile as a colorless liquid.

A 0.2 g. amount of sodium metal is dissolved in 100 ml. of absolute ethanol, then 3.1 g. of phenylhydrazine is added followed by 2.7 g. of 2-hexenecarbonitrile. The reaction mixture is refluxed for 18 hours then is evaporated to dryness *in vacuo*. The residue is dissolved in dichloromethane. The solution is washed with water, dried over anhydrous magnesium sulfate, filtered through a short column of a hydrous magnesium silicate and evaporated to dryness in vacuo to give a tan gum. Hexane is added and the gum solidifies. The tacky solid is collected and dried. The solid is dissolved in ether and concentrated while adding hexane to give 3.3 g. of the product of the Example as light tan crystals, m.p. 118°–120° C.

EXAMPLE 15

3-Amino-1-m-tolyl-2-pyrazoline

A 2.8 g. amount of sodium metal is dissolved in 100 ml. of absolute ethanol, then 15.8 g. of m-tolylhydrazine hydrochloride is added followed in 5 minutes by 9.9 g. of β-ethoxypropionitrile. The reaction mixture is refluxed for 16 hours, then is evaporated to dryness in vacuo. Water is added and the precipitate is collected by filtration. The solid is dissolved in dichloromethane and is passed through a short column of a hydrous magnesium silicate. The column effluent is refluxed on a steam bath with the gradual addition of hexane to crystallize a product. The mixture is cooled and filtered to give 10.1 g. of the product of the Example as colorless crystals, m.p. 119°–120° C.

EXAMPLE 16

3-Amino-5-(3,4-dichlorophenyl)-1-phenyl-2-pyrazoline

A 0.10 g. amount of sodium metal is dissolved in 25.0 ml. of absolute ethanol, then 2.16 g. of phenylhydrazine is added, followed in 5 minutes by 3.96 g. of 3,4-dichlorocinnamonitrile. The reaction mixture is refluxed for 5 hours, then is evaporated to dryness in vacuo. The procedure, as described in Example 15, is continued with a second recrystallization from the same solvent pair and treatment with a hydrous magnesium silicate to give 1.35 g. of the desired product as colorless needles, m.p. 150°–151.5° C.

EXAMPLE 17

3-Amino-5-(p-chlorophenyl)-1-phenyl-2-pyrazoline

A mixture of 500 ml. of absolute ethanol, 5.0 ml. of 50% choline in methanol, 32.4 g. of phenylhydrazine and 49.08 g. of p-chlorocinnamonitrile is refluxed for 7 hours then is allowed to stand at room temperature for 16 hours, then is evaporated to dryness in vacuo. The procedure of Example 16 is followed to give 12.0 g. of the product of the Example as colorless needles, m.p. 183.5°–185.5° C.

EXAMPLE 18

3-Amino-1-(p-methoxyphenyl)-5-phenyl-2-pyrazoline

A 4.42 g. amount of sodium metal is dissolved in 300 ml. of absolute ethanol, then 27.8 g. of p-methoxyphenylhydrazine hydrochloride is added followed in 5 minutes by 20.64 g. of cinnamonitrile. The reaction mixture is refluxed for 7 hours, then is evaporated to dryness in vacuo. Water is added to the residue to give a sludge. The mixture is filtered and the residue is evaporated to dryness. The solid is dissolved in dichloromethane and crystallized as described in Example 16 to give 4.75 g. of the desired product as colorless needles, m.p. 163.5°–166° C.

EXAMPLE 19

3-Amino-5-ethyl-1-phenyl-2-pyrazoline

A 0.23 g. amount of sodium metal is dissolved in 75.0 ml. of absolute ethanol, then 10.8 g. of phenylhydrazine is added, followed in 5 minutes by 3.6 g. of α-methylcrotononitrile. The reaction mixture is refluxed for 18 hours, then is evaporated to dryness in vacuo. Water is added to give a gum which solidifies on standing for 16 hours. The solid is collected and dissolved in dichloromethane. The procedure of Example 15 is continued to give 1.6 g. of the desired product as light yellow crystals, m.p. 123°–125° C.

EXAMPLE 20

4'-(3-Amino-4-methyl-2-pyrazolin-1-yl)-2,2,2-trifluoroacetophenone

A 5.0 g. amount of 3-amino-4-methyl-1-phenyl-2-pyrazoline (Example 4) is combined with 25 ml. of trifluoroacetic anhydride to give an exothermic reaction. The reaction mixture is allowed to stand at room temperature for 24 hours. The precipitate is collected by filtration, dissolved in dichloromethane and evaporated to dryness in vacuo. The residue is dissolved in dichloromethane and the solution is passed through a short column of a hydrous magnesium silicate. The column effluent is refluxed on a stream bath with the gradual addition of hexane to crystallize 5.2 g. of 2,2,2-trifluoro-N-(3-methyl-1-trifluoroacetyl-2-pyrazolin-3-yl)acetamide as pale yellow needles, m.p. 202.5°–204° C.

A 2.0 g. amount of the preceding compound in 150 ml. of absolute methanol is saturated at room temperature with ammonia gas, then is stored in a refrigerator for 16 hours. The reaction mixture is evaporated to dryness in vacuo. The residue is dissolved in dichloromethane and treated with a hydrous magnesium silicate and hexane as previously described to yield 1.6 g. of crude product. This material is chromatographed by preparative column chromatography using silica gel and eluting with acetone:hexane, 50:50, to collect the most polar product. The product is recrystallized from dichloromethane:hexane to give 0.62 g. of the product of the Example as orange needles, m.p. 159°–160° C.

EXAMPLE 21

Preparation of Compressed Tablet

| Ingredient | mg./tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 0.1–5.0 (% w/w) |

EXAMPLE 22

Preparation of Compressed Tablet

| Ingredient | mg./tablet |
| --- | --- |
| Active Compound | 0.5–500 |
| Dibasic Calcium Phosphate N.F. | qs |
| Starch USP | 40 |
| Modified Starch | 10 |
| *Surfactant, e.g. | |
| Sodium Lauryl Sulfate | 0.1–2.0 (% w/w) |
| Magnesium Stearate USP | 0.1–5.0 (% w/w) |

*Other surface active agents such as disodium sulfosuccinate and nonionic surface active agents such as Span ® and Tween ® may also be employed.

EXAMPLE 23

Preparation of Compressed Tablet

| Ingredient | mg./tablet |
| --- | --- |
| Active Compound | 0.5–500 |
| Direct Compression Sugar Agent e.g. Emdex | qs |
| Magnesium Stearate | 0.1–3.0 (% w/w) |

EXAMPLE 24

Preparation of Hard Shell Capsule

| Ingredient | mg./capsule |
| --- | --- |
| Active Compound | 0.5–500 |
| Lactose, Spray Dried | qs |

EXAMPLE 25

Preparation of Oral Liquid (Syrup)

| Ingredient | % w/v |
| --- | --- |
| Active Compound | 0.05-5 |
| Liquid Sugar | 75.0 |
| Methyl Paraben USP | 0.18 |
| Propyl Paraben USP | 0.02 |
| Suspending Agent e.g. Avicel | 0.5-1.0 |
| Flavoring Agent | qs |
| Purified Water qs ad | 100.0 |

EXAMPLE 26

Preparation of Oral Liquid (Elixir)

| Ingredient | % w/v |
| --- | --- |
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 27

Preparation of Oral Suspension (Syrup)

| Ingredient | % w/v |
| --- | --- |
| Active Compound | 0.05-5 |
| Polysorbate 80 USP | 0.1 |
| Magnesium Aluminum Silicate, Colloidal | 0.3 |
| Dye | 0.001-0.5 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 28

Preparation of Injectable Solution

| Ingredient | % w/v |
| --- | --- |
| Active Compound | 0.05-5 |
| Benzyl Alcohol N.F. | 0.9 |
| Water for Injection | 100.0 |

EXAMPLE 29

Preparation of Injectable Oil

| Ingredient | % w/v |
| --- | --- |
| Active Compound | 0.05-5 |
| Benzyl Alcohol | 1.5 |
| Sesame Oil qs ad | 100.0 |

EXAMPLE 30

Preparation of Intra-articular Product

| Ingredient | Amount |
| --- | --- |
| Active Compound | 2-20 mg. |
| NaCl (physiological saline) | 0.9% |
| Benzyl Alcohol | 0.9% |
| Sodium Carboxymethylcellulose pH adjusted to 5.0-7.5 | 1-5% |
| Water for Injection qs ad | 100% |

EXAMPLE 31

Preparation of Injectable Depo Suspension

| Ingredient | % w/v |
| --- | --- |
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

EXAMPLE 32

Preparation of Topical Cream

| Ingredient | % w/v |
| --- | --- |
| Active Compound | 0.05-5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 33

Preparation of Topical Ointment

| Ingredient | % w/w |
| --- | --- |
| Active Compound | 0.05-5 |
| Cholesterol | 3 |
| Stearyl Alcohol | 3 |
| White Wax | 8 |
| Petrolatum, White USP qs | 100 |

We claim:

1. The compound, 3-amino-1-(4-biphenylyl)-5-methyl-2-pyrazoline.

2. The compound, 3-amino-5-(3,4-dichlorophenyl)-1-phenyl-2-pyrazoline.

3. The compound, 4'-(3-amino-4-methyl-2-pyrazoline-1-yl)-2,2,2-trifluoroacetophenone.

* * * * *